United States Patent [19]

Guglielmetti

[11] Patent Number: 5,041,632
[45] Date of Patent: Aug. 20, 1991

[54] PROCESS FOR THE PREPARATION OF 4,4'-DINITROSTILBENE-2,2-DISULFONIC ACID

[75] Inventor: Leonardo Guglielmetti, Bottmingen, Switzerland

[73] Assignee: Ciba-Geigy Corporation, Ardsley, N.Y.

[21] Appl. No.: 203,850

[22] Filed: Jun. 7, 1988

[30] Foreign Application Priority Data

Aug. 12, 1987 [CH] Switzerland ............. 3098/87
Oct. 29, 1987 [CH] Switzerland ............. 4228/87
Mar. 25, 1988 [CH] Switzerland ............. 1142/88

[51] Int. Cl.$^5$ .................................... C07C 307/00
[52] U.S. Cl. ............................................. 562/60
[58] Field of Search .................. 260/505 R; 562/60

[56] References Cited

U.S. PATENT DOCUMENTS 4,680,146 7/1987 Skipka et al. ............. 260/505 R
4,719,051 1/1988 Guglielmetti ............. 260/505 R

FOREIGN PATENT DOCUMENTS 26154 2/1980 European Pat. Off. .
106961 9/1897 Fed. Rep. of Germany .
113514 12/1897 Fed. Rep. of Germany .
2258530 11/1972 Fed. Rep. of Germany .
3409171 3/1984 Fed. Rep. of Germany .
3519552 5/1985 Fed. Rep. of Germany .
240200 10/1986 German Democratic Rep. .
2136430 7/1984 United Kingdom ............ 260/505 R

OTHER PUBLICATIONS

Chemische Berichte vol. 30, pp. 3097–3101 (1897); vol. 31, p. 1079 (1898).
Chemisches Zentralblatt vol. 1900 I, 1085.
Chemisches Zentralblatt vol. 1900 II, 703.
C.A. 83, 113,377k (1975).
C.A. 85, 192,288z, 192,289a, 192,290u (1976).
C.A. 86, 16029c (1977).
Chimie Analytique 50, pp. 251–254 (1968).
Chemie et Industrie, Genie Chimique 101, pp. 1439–1447 (1969).

Primary Examiner—Alan Siegel
Attorney, Agent, or Firm—Kevin T. Mansfield; Edward McC. Roberts

[57] ABSTRACT

A process is described for the preparation of 4,4'-dinitrostilbene-2,2'-disulfonic acid by oxidation of 4-nitrotoluene-2-sulfonic acid by using liquid, anhydrous ammonia, a liquid alkyl derivative of ammonia or a mixture of ammonia and/or the alkyl derivatives of ammonia with water as the solvent.

16 Claims, No Drawings

PROCESS FOR THE PREPARATION OF 4,4'-DINITROSTILBENE-2,2-DISULFONIC ACID

This application relates to a novel process for the preparation of 4,4'-dinitrostilbene-2,2'-disulfonic acid.

Processes for the industrial preparation of 4,4'-dinitrostilbene-2,2'-disulfonic acid (DNS) and salts thereof are generally known and consist in the oxidative condensation of 2 mol of 4-nitrotoluene-2-sulfonic acid (p-NTSA) under aqueous alkaline conditions by the old methods developed towards the end of the last century. The oxidizing agents described are oxygen (air) in the presence of a catalyst or sodium hypochlorite (cf., for example, A. G. Green and A. R. Wahl, Chemische Berichte 30, 3097–3101 (1897); 31, 1079 (1898); DRP 106,961; Chemisches Zentralblatt 1900 I, 1085; DRP 113,514 and Chemisches Zentralblatt 1900 II, 703). However, these processes give 4,4'-dinitrostilbene-2,2'-disulfonic acid and salts thereof, despite modern technical improvements, only in relatively poor yields, which are between 60 and 75% (cf., for example, DE Offenlegungsschrift 2,258,530).

In the last 25 years, a large number of efforts have therefore been undertaken to improve the yield of this condensation by applying physico-chemical, mathematical and analytical methods and also computer models. However, these efforts have not resulted in a successful breakthrough [cf., for example, C.A. 83, 113,377 k (1975); C.A. 85, 192,288 z, 192,289a, 192,290 u (1976); C.A. 86, 16029c (1977); Chimie Analytique 50, 251–254 (1968) and Chimie et Industrie, Genie Chimique 101, 1439–1447 (1969)].

The efforts which may be mentioned in particular are those undertaken in the last 10 years, virtually all of which had the objective of solving the huge ecological problems, for example the non-biodegradable mother liquors, by optimization of the yield.

Thus, according to DD Patent 240,200, the aqueous air oxidation of 4-nitrotoluene-2-sulfonic acid is carried out in two steps and at two different temperatures and two different alkali concentrations, some of the 4,4'-dinitrodibenzyl-2,2'-disulfonic acid precipitating in the first step. The yields of 4,4'-dinitrostilbene-2,2'-disulfonic acid are reported as 82 to 85% of theory, but without any statement about the quality of the material obtained.

DE Offenlegungsschrift 3,409,171 discloses a process in which the aqueous air oxidation of 4-nitrotoluene-2-sulfonic acid is carried out in the presence of lithium ions and hydroxyl ions and in the presence or absence of a catalyst. The yields given of 4,4'-dinitrostilbene 2,2'-disulfonic acid are about 80 to 90% of theory. The disadvantage of this process is the additional step of separating off the lithium as lithium carbonate before isolating the 4,4'-dinitrostilbene-2,2'-disulfonic acid, the recovery of lithium carbonate being only 75 to 83%. In addition, the recovered lithium carbonate first has to be converted to lithium hydroxide before it can be recycled into the process.

German Offenlegungsschrift 3,519,552 describes a process for the preparation of 4,4'-dinitrostilbene-2,2'-disulfonic acid salts by aqueous air oxidation of 4-nitrotoluene-2-sulfonic acid, which comprises adding during the reaction potassium ions, calcium ions and/or magnesium ions at the rate at which 4,4'-dinitrostilbene-2,2'-disulfonic acid is formed, the amount of the potassium ions, calcium ions and/or magnesium ions being 10 to 150 mol %, based on the amount of 4,4'-dinitrostilbene-2,2'-disulfonic acid which is, in each case, present in the reaction mixture, at each point of the reaction and separating off the precipitated salt of the 4,4'-dinitrostilbene-2,2'-disulfonic acid. The disadvantage of this process is the workup and the disposal of the large amounts of base and of the potassium salts, calcium salts and magnesium salts which had been added in large amounts.

European Patent Application 26,154 describes a process for the preparation of 4,4'-dinitrostilbene-2,2'-disulfonic acid and salts thereof by air oxidation of 4-nitrotoluene-2-sulfonic acid in organic solvents. In this process, yields of not more than 96% of theory are obtained depending on the procedure. The disadvantage of this process is the working with aprotic dipolar solvents whose recovery is complicated and as is known cannot be carried out without losses.

It has now been found that 4,4'-dinitrostilbene-2,2'-disulfonic acid (DNS) and salts thereof can surprisingly be prepared in high yields without the abovementioned disadvantages by oxidation of 4-nitrotoluene2-sulfonic acid with an oxidizing agent by performing the oxidation in liquid, anhydrous ammonia, in an alkyl derivative thereof in the presence or absence of water and/or mixtures of these solvents in one another.

Accordingly, this application provides a process for the preparation of 4,4'-dinitrostilbene-2,2'-disulfonic acid and salts thereof of the formula

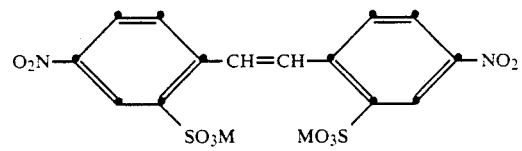

in which M is hydrogen, an alkali metal cation or an ammonium cation, by oxidation of 4-nitrotoluene-2-sulfonic acid or salts thereof with an oxidizing agent, which comprises performing the oxidation in liquid, anhydrous ammonia, in an alkyl derivative thereof in the absence or presence of water and/or mixtures of these solvents in one another and in the presence of strong bases and in the absence or presence of catalysts.

The starting material 4-nitrotoluene-2-sulfonic acid (p-NTSA) or alkali metal salts and ammonium salts thereof is a compound known in the chemical industry, which can be prepared very easily by sulfonation of 4-nitrotoluene. It can be used either as the free acid or as one of its known salts. These salts can be used either in dry form or, preferably, also as a moist pressed cake having a water content of 1 to 50%, preferably 1 to 25%, or in the form of another precursor such as the synthesis solution or suspension, the concentrated aqueous preparation, as a water-containing oil or even as a dry powder.

Liquid, anhydrous ammonia, an alkyl derivative thereof in the absence or presence of water and/or mixtures of these solvents in one another, which are used as reaction solvents in the present process according to the invention, are to be understood as meaning in particular the following solvents or combinations:

a) anhydrous, liquid ammonia b) an anhydrous, liquid alkyl derivative of ammonia c) a mixture of a) and b)

d) ammonia and water, e) an alkyl derivative of ammonia and water, f) ammonia and an alkyl derivative of ammonia and water.

Preference is given to the combination d).

Not only 4-nitrotoluene-2-sulfonic acid which is used as the starting material but also 4,4'-dinitrodibenzyl-2,2'-disulfonic acid which is formed as an intermediate and the reaction product 4,4'-dinitrostilbene-2,2'-disulfonic acid are more soluble, for example among the reaction media mentioned in this process, in the abovementioned solvents or combinations a) to f) and in particular in the combination d) than in water or aprotic dipolar solvents. Therefore, the reaction which is carried out today in industry in high dilution can be carried out in a more concentrated solution, for example even with one part of the solvents or combinations a) to f) mentioned per part of 4-nitrotoluene-2-sulfonic acid, preferably with 1–10 parts and in particular 3–6 parts of one of the solvents or combinations a) to f) mentioned; this fact is a great advantage industrially and economically. Furthermore, ammonia is cheap and readily available on a large industrial scale. By virtue of its low boiling point (−33.35° C. at 760 torr) and its high stability under the reaction conditions mentioned in this process, it can be recovered virtually quantitatively and can therefore be recycled into the process.

Alkyl derivatives of ammonia can be both primary and secondary and tertiary amines of the following formulae:

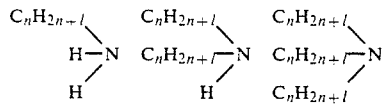

in these formulae, n is in particular the numbers 1 to 6, these amines being not only uniform amines (for example dimethylamine) but also mixed amines (for example ethyldimethylamine). Particular preference is given to dimethylamine, trimethylamine, ethylamine, diethylamine, triethylamine and, in particular, methylamine.

The combinations d) to f) used as reaction solvents in the process according to the invention preferably contain 50 to 99% and, in particular, 60 to 80% of ammonia and/or an alkyl derivative of ammonia, based on the total amount of the corresponding combination. The ratio of water to ammonia here can be adjusted in various ways, for example by initially introducing water, an aqueous ammonia solution having, for example, an ammonia content of 1 to 30%, aqueous 4-nitrotoluene-2-sulfonic acid or salts thereof or liquid ammonia and then adding the missing parts of ammonia, water, base dissolved in water, aqueous ammonia or alkyl derivatives of ammonia.

Strong bases are in particular the alkali metals or alkaline earth metals such as lithium, sodium, potassium, magnesium and calcium and also their strongly basic compounds, for example hydroxides, amides, alcoholates, and also strongly basic ion-exchangers.

The alcoholates used are essentially those which are derived from open-chain, branched or cyclic lower aliphatic alcohols having 1 to 8 carbon atoms, preferably 1 to 4 carbon atoms, such as methanol, ethanol, propanol, butanol, isopropanol and tert-butanol. These alcoholates are preferably used in the form of the corresponding alcoholic solution.

Preferably, sodium compounds or potassium compounds are used, hydroxides and alcoholates thereof being of particular practical importance.

Depending on the type and amount of the base used, it is advantageous to use the base dissolved in a protic solvent. The preferred protic solvents used are water or open-chain, branched or cyclic low-molecular-weight aliphatic alcohols having 1 to 8 carbon atoms. The use of methanol and/or water is particularly important.

In carrying out the oxidation, the base can either be initially introduced into the reaction vessel, p-NTSA being metered in or it can be metered in at the same time as p-NTSA but through separate metering units, or it can be metered in by itself to the initially introduced p-NTSA.

The amount of base to be used can vary within wide limits. In the presence of a catalyst, catalytic amounts can be used since the base is regenerated during the course of the reaction. However, preferably the amounts of base used are, based on p-NTSA, between catalytic and equivalent amounts, in particular 0.25 to 0.5 mole. In the absence of a catalyst, the oxidation is carried out by using at least equivalent amounts of base, based on p-NTSA. However, the optimum amount of base to be used can easily be determined by preliminary tests.

The catalysts can be salts, oxides of hydroxides or heavy-metal compounds and/or organometallic compounds of heavy metals, for example those of Co. Mn, Cr, Ce, Fe, Ni, Cu, Ru, Pd, Pt or Ir (cf., for example, Homogeneous Catalysis by Metal Complexes, Vol. I, Chapter 2: Activation of molecular oxygen, page 79, Academic Press New York and London 1974). However, catalysts which are of particular importance are the salts, oxides or hydroxides of manganese and/or the organomanganese compounds, for example manganese sulfate and/or manganese acetate.

It can also be advantageous to use inorganic or organic bromine and/or iodine compounds, for example NaI, KI, KBr and ammonium bromide.

Furthermore, phase transfer catalysts or crown ethers can also be additionally used, particularly in those cases in which the strong bases to be used have an insufficient solubility in liquid ammonia.

Examples of phase transfer catalysts are: ammonium chloride, ammonium bromide, methylamine hydrochloride, cyclohexylamine hydrochloride, aniline hydrochloride, dimethylamine hydrochloride, di-isobutylamine hydrochloride, triethylamine hydrochloride, triethylamine hydrobromide, tri-n-octylamine hydrochloride, benzyldimethylamine hydrochloride, tetramethylammonium, tetraethylammonium, tetra-n-propylammonium, tetra-n-butylammonium chloride, bromide and iodide, trimethylhexadecylammonium chloride, benzyldimethylhexadecylammonium chloride, benzyldimethyltetradecylammonium chloride, benzyltrimethylamonium, benzyltriethylammonium and benzyltri-n-butylammonium chloride, n-butyl-tri-n-propylammonium bromide, octadecyltrimethylammonium bromide, phenyltrimethylammonium bromide or chloride, hexadecylpyridinium bromide and chloride.

Examples of crown ethers are: 15-crown-5; 18-crown-6; dibenzo-18-crown6; dicyclohexyl-18-crown-6; 5,6,14,15-dibenzo-7,13-diaza-1,4-dioxacyclopentadeca-5,14-diene.

The amount of catalysts used can vary within wide limits. In some cases, trace amounts of catalysts are sufficient. However, in general the catalysts are preferably used in an amount of about 0.1 to 15 percent by weight, based on 4-nitrotoluene-2-sulfonic acid or salts thereof.

In general, the reaction temperature is not critical and can be between −33° C. and +50° C., however, preferably it is between −15° C. and 30° C., in particular between 0° C. and 25° C. If the reaction is carried out at −33° C., it takes place at atmospheric pressure. At higher temperatures, the reaction must be carried out at the vapour pressure of liquid ammonia, of the alkyl derivative of ammonia or of the mixture of ammonia and/or the alkyl derivative of ammonia with water in question which is known from the literature (Encylopedia of Chemical Technology, Third Edition, Volume 2, Page 474; Ullmanns Encyklopädie der Technischen Chemie (Ullmann's Encyclopaedia of Industrial Chemistry), 1953, Volume 3, Page 524).

The oxidizing agent can be pure oxygen or mixtures thereof with inert gases, for example nitrogen, and air. The oxidizing agents are used in excess relative to p-NTSA. In general, an excess of about 300%, preferably 50% to 100% relative to p-NTSA is used. Of particular practical importance is the use of pure oxygen in a closed circuit, the oxygen consumed being constantly replaced.

In a preferred embodiment, one part of 4-nitrotoluene-2-sulfonic acid or salts thereof in the form of a moist presscake is suspended together with a catalytic amount of manganese (II) salt such as manganese sulfate and/or manganese acetate in 0.5 to 3 parts of aqueous ammonia solution or water and treated with 1 to 5 parts of liquid ammonia, bringing the ammonia content of the entire reaction mixture to 60% to 80%, and is reacted in the presence of oxygen as the oxidizing agent and sodium hydroxide as the base at temperatures from 0°–25° C. and under pressure. The workup is carried out in a known manner.

The process according to the invention provides the 4,4'-dinitrostilbene-2,2'-disulfonic acid or salts thereof in almost quantitative yield and high purity without the formation of coloured biproducts.

A further advantage of the process is that the DNS prepared according to the invention can directly be reduced further without additional purification and, where liquid ammonia was used, even without workup to give (4-amino-4'-nitro)-stilbene-2,2'-disulfonic acid and 4,4'-diaminostilbene-2,2'-disulfonic acid, an important intermediate for the preparation of dyes and fluorescent brighteners. This reduction is carried out in a manner known per se using hydrogen in the presence of catalysts.

The following examples illustrate the invention without limiting it thereto. Parts and percentages are by weight.

EXAMPLE 1

In a 1-liter BUECHI glass autoclave equipped with cooling/heating jacket, manometer, gas introduction stirrer, thermometer, dropping funnel, gas introduction dip tube, two one-way valves and two rotameters for introduction and removal of oxygen and burst disc (10 bar), 97.0 g of sodium 4-nitrotoluene-2-sulfonate (active content: 98.6%), 4.5 g of manganese (II) acetate tetrahydrate and 360 g of liquid ammonia are initially introduced at −40° C. and atmospheric pressure—this corresponds to a ratio of 1 part of the sodium salt of p-NTSA to 3.8 parts of ammonia.

The autoclave is sealed, and the internal temperature of −33.3° C. is increased to +5° C., increasing the internal pressure to 4 bar.

An oxygen stream of 10 l/h is introduced into the resulting clear solution at a stirrer speed of 600 to 700 r.p.m. In addition, 21.6 g of a methanolic 30% sodium methylate solution are added over a period of 20 minutes at an internal temperature of 5° to 7° C. The resulting reaction mixture is stirred for an hour and 40 minutes at 5° C., while oxygen (10 l/h) is introduced.

For workup, the internal pressure in the autoclave is reduced from 4 bar to atmospheric pressure by partial evaporation of ammonia, resulting in a decrease of the internal temperature from +5° C. to −27° C. The reaction mixture is then treated with 6.5 g of ammonium chloride at atmospheric pressure and slowly diluted with 400 ml of methanol, in the course of which the reaction product precipitates as crystals. The oxygen stream is turned off, and the resulting suspension is freed from ammonia by slowly heating to +30° C. The stirrer is turned off, and the autoclave is emptied.

The reaction mixture is evaporated to dryness under vacuum, taken up in 2 l of water, made alkaline with 200 ml of 2N sodium hydroxide solution, neutralized with 200 ml of 2N hydrochloric acid, freed from the catalyst by filtration, and the resulting light yellow solution is evaporated to dryness under vacuum. The residue is taken up in 300 ml of water, and the reaction product is precipitated from this solution by the addition of 34 g of sodium chloride, filtered off with suction, washed with 100 ml of a 7.5% sodium chloride solution and dried under vacuum at 110° C. until the weight remains constant. This gives 95.0 g of disodium 4,4'-dinitrostilbene-2,2'-disulfonate in the form of a light yellow crystalline powder of melting point above 300° C., which has an active content (determined by UV spectrophotometry) of 94.0%. The yield of disodium 4,4'-dinitrostilbene-2,2'-disulfonate is 94.1% of theory. The yield of disodium 4,4'-dinitrostilbene-2,2'-disulfonate determined by LC analysis is 93.6% of theory.

EXAMPLE 2

In a glass autoclave according to Example 1, 97.0 g of sodium 4-nitrotoluene-2-sulfonate (active content: 98.6%), 3.1 g of manganese (II) sulfate monohydrate and 360 g of liquid ammonia are initially introduced at atmospheric pressure and at −40° C.—this corresponds to a ratio of 1 part of the sodium salt of p-NTSA to 3.8 parts of ammonia. The autoclave is sealed, and the internal temperature is increased from −33.3° C. to +15° C., resulting in an increase of the internal pressure to 6 bar.

An oxygen stream of 10 l/h is introduced into the resulting clear solution at a stirrer speed of 600 to 700 r.p.m. In addition, 11 g of a methanolic 30% sodium methylate solution are added over a period of 25 minutes at an internal temperature of 15° C. The resulting reaction mixture is stirred for an hour and 35 minutes at 15° C., while oxygen (10 l/h) is introduced.

The workup is carried out as described in Example 1, except that the reaction mixture is treated with 4.5 g of ammonium chloride. This gives 96.2 g of disodium 4,4'-dinitrostilbene-2,2'-disulfonate in the form of a light yellow crystalline powder of melting point above 300° C., which has an active content (determined by UV spectrophotometry) of 91.7%. The yield of disodium 4,4'-dinitrostilbene-2,2'-disulfonate is 93.0% of theory.

Similar results are obtained by performing the reaction in a ratio of 1 part of the sodium salt of p-NTSA to 2.5 parts of ammonia.

EXAMPLE 3

In a 1-liter BUECHI glass autoclave equipped with cooling/heating jacket, manometer, gas introduction stirrer, thermometer, dropping funnel, gas introduction tube above the fill level, two one-way valves and two rotameters for introduction and removal of oxygen and burst disc (10 bar), 97.0 g of sodium 4-nitrotoluene-2-sulfonate (active content: 98.6%), 4.6 g of manganese (II) nitrate tetrahydrate and 375 g of liquid ammonia are initially introduced at −40° C. and atmospheric pressure—this corresponds to a ratio of 1 part of the sodium salt of p-NTSA to 3.9 parts of ammonia. The autoclave is sealed, and the internal temperature of −33.3° C. is increased to +15° C., increasing the internal pressure to 6 bar.

An oxygen stream of 13 l/h is introduced above the level of the resulting clear solution at a stirrer speed of 600 to 700 r.p.m. In addition, a solution of 4.8 g of sodium hydroxide in 24 g of methanol are added over a period of 30 minutes at an internal temperature of 15° C. The resulting reaction mixture is stirred for an hour at 15° C., while oxygen (13 l/h) is introduced.

The workup is carried out as described in Example 1. This gives 97.2 g of disodium 4,4'-dinitrostilbene-2,2'-disulfonate in the form of a light yellow crystalline powder of melting point above 300° C., which has an active content (determined by UV spectrophotometry) of 89.1%. The yield of disodium 4,4'-dinitrostilbene-2,2'-disulfonate is 91.3% of theory.

EXAMPLE 4

In a glass autoclave according to Example 3, 97.0 g of sodium 4-nitrotoluene-2-sulfonic acid (active content: 98.6%), 4.5 g of manganese (II) acetate tetrahydrate and 360 g of liquid ammonia are initially introduced at atmospheric pressure and at −40° C. The autoclave is sealed, and the internal temperature increases from −33.3° C. to +15° C., resulting in an increase of the internal pressure to 6 bar.

An oxygen stream of 13 l/h is introduced above the level of the resulting clear solution at a stirrer speed of 600 to 700 r.p.m. In addition, 19.2 g of a 50% aqueous sodium hydroxide solution are added over a period of 15 minutes at an internal temperature of 15° C. The resulting reaction mixture contains an ammonia/water mixture of 97.5% of ammonia and 2.5% of water (this corresponds to a ratio of 1 part of the sodium salt of p-NTSA to 3.9 parts of the solvent mixture). The resulting reaction mixture is stirred for one hour and 15 minutes at 15° C., while oxygen (13 l/h) is introduced.

The workup is carried out as described in Example 1. This gives 95.2 g of disodium 4,4'-dinitrostilbene-2,2'-disulfonate in the form of a light yellow crystalline powder of melting point above 300° C., which has an active content (determined by UV spectrophotometry) of 93.5%. The yield of disodium 4,4'-dinitrostilbene-2,2'-diuulfonate is 93.8% of theory. The yield of disodium 4,4'-dinitrostilbene-2,2'-disulfonic acid determined by LC analysis is 92.8% of theory.

EXAMPLE 5

In a glass autoclave according to Example 1, 97.0 g of sodium 4-nitrotoluene-2-sulfonic acid (active content: 98.6%), 4.5 g of manganese (II) acetate tetrahydrate and 360 c of liquid ammonia are initially introduced at atmospheric pressure and at −40° C. The autoclave is sealed, and the internal temperature increased from −33.3° C. to +15° C., resulting in an increase of the internal pressure to 6 bar.

An oxygen stream of 13 l/h is introduced to the resulting clear solution at a stirrer speed of 600 to 700 r.p.m. In addition, 16.0 g of a 30% aqueous sodium hydroxide solution are added over a period of 15 minutes at an internal temperature of 15° to 17° C. The resulting reaction mixture contains an ammonia/water mixture of 97% of ammonia and 3% of water (this corresponds to a ratio of 1 part of the sodium salt of p-NTSA to 3.9 parts of the solvent mixture). The resulting reaction mixture is stirred for 45 minutes at 15° C., while oxygen (13 l/h) is introduced.

The workup is carried out as described in Example 1. This gives 97.0 g of disodium 4,4'-dinitrostilbene-2,2'-disulfonate in the form of a light yellow crystalline powder of melting point above 300° C., which has an active content (determined by UV spectrophotometry) of 92.2%. The yield of disodium 4,4'-dinitrostilbene-2,2'-disulfonate is 94.3% of theory. The yield of disodium 4,4'-dinitrostilbene-2,2'-disulfonic acid deterained by LC analysis is 95.0% of theory.

EXAMPLE 6

In a glass autoclave according to Example 3, 97.0 g of sodium 4-nitrotoluene-2-sulfonic acid (active content: 98.6%), 3.1 g of manganese (II) sulfate monohydrate and 360 g of liquid ammonia are initially introduced at atmospheric pressure and at −40° C. The autoclave is sealed, and the internal temperature increases from −33.3° C. to 15° C., resulting in an increase of the internal presssure to 6 bar.

An oxygen stream of 13 l/h is introduced above the level of the resulting clear solution at a stirrer speed of 600 to 700 r.p.m. In addition 32 g of a 15% aqueous sodium hydroxide solution are added over a period of 15 minutes at an internal temperature of 15° C. to 17° C. The resulting reaction mixture contains an ammonia/water mixture of 93% of ammonia and 7% of water (this corresponds to a ratio of 1 part of the sodium salt of p-NTSA to 4.1 parts of the solvent mixture). The resulting reaction mixture is stirred for 45 minutes at 15° C., while oxygen (13 l/h) is introduced.

The workup is carried out as described in Example 1. This gives 94.4 g of disodium 4,4'-dinitrostilbene-2,2'-disulfonate in the form of a light yellow crystalline powder of melting point above 300° C., which has an active content (determined by UV spectrophotometry) of 96.1%. The yield of disodium 4,4'-dinitrostilbene-2,2'-disulfonate is 95.6% of theory. The yield of disodium 4,4'-dinitrostilbene-2,2'-disulfonic acid of the reaction mixture before workup as determined by LC analysis is 96.4% of theory.

EXAMPLE 7

In a glass autoclave according to Example 3, 97.0 g of sodium 4-nitrotoluene-2-sulfonic acid (active content: 98.6%) 4.6 g of manganese (II) nitrate tetrahydrate and 360 g of liquid ammonia are initially introduced at atmospheric pressure and at −40° C. The autoclave is sealed, and the internal temperature increases from −33.3° C. to +15° C., resulting in an increase of the internal pressure to 6 bar.

An oxygen stream of 13 l/h is introduced above the level of the resulting clear solution at a stirrer speed of 600 to 700 r.p.m. In addition, 64 g of a 7.5% aqueous sodium hydroxide solution are added over a period of 15 minutes at an internal tempertture of 15° C. to 20° C. The resulting reaction mixture contains an ammonia/water mixture of 86% of ammonia and 14% of water (this corresponds to a ratio of 1 part of the sodium salt of p-NTSA to 4.4 parts of the solvent mixture). The resulting reaction mixture is stirred for 45 minutes at 15° C., while oxygen (13 l/h) is introduced.

The workup is carried out as described in Example 1. This gives 93.4 g of disodium 4,4'-dinitrostilbene-2,2'-disulfonate in the form of a light yellow crystalline powder of melting point above 300° C., which has an active content (determined by UV spectrophotometry) of 96.9%. The yield of disodium 4,4'-dinitrostilbene-2,2'-disulfonate is 95.4% of theory. The yield of disodium 4,4'-dinitrostilbene-2,2'-disulfonic acid determined by LC analysis is 94.7% of theory.

EXAMPLE 8

In a glass autoclave according to Example 3, 77.6 g of sodium 4-nitrotoluene-2-sulfonic acid (active content: 98.6%), 1.6 g of manganese (II) acetate tetrahydrate and 66 g of a 25% aqueous ammonia solution are initially introduced at atmospheric pressure. The autoclave is sealed, and at an internal temperature of 15° C. 242 g of liquid ammonia are added, resulting in an increase of the internal pressure to 4.4 bar.

An oxygen stream of 10 l/h is introduced above the level of the resulting clear solution at a stirrer speed of 600 to 700 r.p.m. In addition 42.7 g of a 30% aqueous sodium hydroxide solution are added over a period of 20 minutes at an internal temperature of 15° C. to 17° C. The resulting reaction mixture contains an ammonia/water mixture of 76.5% of ammonia and 23.5% of water (this corresponds to a ratio of 1 part of the sodium salt of p-NTSA to 4.4 parts of the solvent mixture). The resulting reaction mixture is stirred for 2 hours at 15° C., while oxygen (10 l/h) is introduced.

The workup is carried out as described in Example 1 except that the reaction mixture is treated with 17 g of ammonium chloride and is diluted with 100 ml of water instead of methanol. This gives 75.4 g of disodium 4,4'-dinitrostilbene-2,2'-disulfonate in the form of a light yellow crystalline powder of melting point above 300° C., which has an active content (determined by UV spectrophotometry) of 96.7%. The yield of disodium 4,4'-dinitrostilbene-2,2'-disulfonate is 96.0% of theory. The yield of disodium 4,4'-dinitrostilbene-2,2'-disulfonic acid of the reaction mixture before workup as determined by LC analysis is 96.5% of theory.

EXAMPLE 9

In an autoclave according to Example 1, 97.0 g of sodium 4-nitrotoluene-2-sulfonic acid (active content: 98.6%) 94.4 g of water, 4.5 g of manganese (II) acetate tetrahydrate and 266 g of liquid ammonia are initially introduced at atmospheric pressure and at −40° C. The autoclave is sealed, and the internal temperature increased from −33.3° C. to +13° C., resulting in an increase of the internal pressure to 3.3 bar.

An oxygen stream of 10 l/h is introduced to the resulting clear solution at a stirrer speed of 600 to 700 r.p.m. In addition, 16.0 g of a 30% aqueous sodium hydroxide solution are added over a period of 15 minutes at an internal temperature of 13° to 15° C. The resulting reaction mixture contains an ammonia/water mixture of 71.5% of ammonia and 28.5% of water (this corresponds to a ratio of 1 part of the sodium salt of p-NTSA to 3.9 parts of the solvent mixture). The resulting reaction mixture is stirred for 45 minutes at 15° C., while oxygen (10 l/h) is introduced.

The workup is carried out as described in Example 1 except that 300 ml of water are used instead of 400 ml of methanol. This gives 96.3 g of disodium 4,4'-dinitrostilbene-2,2'-disulfonate in the form of a light yellow crystalline powder of melting point above 300° C., which has an active content (determined by UV spectrophotometry) of 91.6%. The yield of disodium 4,4'-dinitrostilbene-2,2'-disulfonate is 93.0% of theory. The yield of disodium 4,4'-dinitrostilbene-2,2'-disulfonic acid determined by LC analysis is 92.8% of theory.

Using instead of 97.0 g of sodium 4-nitrotoluene-2-sulfonate, 115.1 g of this compound as a moist presscake (active content: 83.1%; water content: 15.7%) and correspondingly 76.3 g of water, the same results are obtained.

EXAMPLE 10

In a glass autoclave according to Example 3, 97.0 g of sodium 4-nitrotoluene-2-sulfonic acid (active content: 98.6%) 2 g of manganese (II) acetate tetrahydrate and 195 g of a 25% aqueous ammonia solution are initially introduced at atmospheric pressure. The autoclave is sealed, and at an internal temperature of 15° C. 210 g of liquid ammonia are added, resulting in an increase of the internal pressure to 2.6 bar.

An oxygen stream of 10 l/h is introduced above the level of the resulting clear solution at a stirrer speed of 600 to 700 r.p.m. In addition, 26.7 g of a 30% aqueous sodium hydroxide solution are added over a period of 20 minutes at an internal temperature of 10° C. to 15° C. The resulting reaction mixture contains an ammonia/water mixture of 61% of ammonia and 39% of water (this corresponds to a ratio of 1 part of the sodium salt of p-NTSA to 4.4 parts of the solvent mixture). The resulting reaction mixture is stirred for 2 hours at 15° C., while oxygen (10 l/h) is introduced.

The workup is carried out as described in Example 1 except that the reaction mixture is treated with 11 g of ammonium chloride and is diluted with 100 ml of water instead of methanol. This gives 95.4 g of disodium 4,4'-dinitrostilbene-2,2'-disulfonate in the form of a light yellow crystalline powder of melting point above 300° C., which has an active content (determined by UV spectrophotometry) of 92.4%. The yield of disodium 4,4'-dinitrostilbene−2,2'-disulfonate is 92.9 % of theory. The yield of disodium 4,4'-dinitrostilbene-2,2'-disulfonic acid of the reaction mixture before workup as determined by LC analysis is 95.7% of theory.

Using, instead of 97.0 g of sodium 4-nitrotoluene-2-sulfonate, 1115.1 g of this compound as a moist pressed cake (active content: 83.1%; water content: 15.7%) and correspondingly 171 g of a 25% aqueous ammonia solution and 216 g of liquid ammonia, the same results are obtained.

EXAMPLE 11

In a glass autoclave according to Example 3, 77.6 g of sodium 4-nitrotoluene-2-sulfonic acid (active content: 98.6%) 1.6 g of manganese (II) acetate tetrahydrate and 202 g of a 25% aqueous ammonia solution are initially introduced at atmospheric pressure. The autoclave is sealed, and at an internal temperature of 20° C. 210 g of liquid ammonia are added, resulting in an increase of the internal pressure to 4 b.r.

An oxygen stream of 10 l/h is introduced above the level of the resulting clear solution at a stirrer speed of 600 to 700 r.p.m. In addition 21.3 g of a 30% aqueous sodium hydroxide solution are added over a period of 20 minutes at an internal temperature of 18° C. to 20° C. The resulting reaction mixture contains an ammonia/water mixture of 61% of ammonia and 39% of water (this corresponds to a ratio of 1 part of the sodium salt of p-NTSA to 5.6 parts of the solvent mixture). The resulting reaction mixture is stirred for 2 hours at 20° C., while oxygen (10 l/h) is introduced.

The workup is carried out as described in Example 1 except that the reaction mixture is treated with 9 g of ammonium chloride and is diluted with 100 ml of water instead of methanol. This gives 76.8 g of disodium 4,4'-dinitrostilbene-2,2'-disulfonate in the form of a light yellow crystalline powder of melting point above 300° C., which has an active content (determined by UV spectrophotometry) of 94.8%. The yield of disodium 4,4'-dinitrostilbene-2,2'-disulfonate is 95.9 % of theory. The yield of disodium 4,4'-dinitrostilbene-2,2'-disulfonic acid of the reaction mixture before workup as determined by LC analysis is 96.5% of theory.

Similar results are obtained by performing the reaction in a ratio of 1 part of the sodium salt of p-NTSA to 8 parts of the solvent mixture.

EXAMPLE 12

In a glass autoclave according to Example 3, 77.6 g of sodium 4-nitrotoluene-2-sulfonic acid (active content: 98.6%), 1.6 g of manganese (II) acetate tetrahydrate and 148 g of a 25% aqueous ammonia solution are initially introduced at atmospheric pressure. The autoclave is sealed, and at an internal temperature of 15° C. 172 g of liquid ammonia are added, resulting in an increase of the internal pressure to 3.5 bar.

An oxygen stream of 10 l/h is introduced above the level of the resulting clear solution at a stirrer speed of 600 to 700 r.p.m. In addition 32 g of a 30% aqueous sodium hydroxide solution are added over a period of 20 minutes at an internal temperature of 10° C. to 15° C. The resulting reaction mixture contains an ammonia/water mixture of 61% of ammonia and 39% of water (this corresponds to a ratio of 1 part of the sodium salt of p-NTSA to 4.5 parts of the solvent mixture). The resulting reaction mixture is stirred for 2 hours at 15° C., while oxygen (10 l/h) is introduced.

The workup is carried out as described in Example 1 except that the reaction mixture is treated with 12.8 g of ammonium chloride and is diluted with 100 ml of water instead of methanol. This gives 78.2 g of disodium 4,4'-dinitrostilbene-2,2'-disulfonate in the form of a light yellow crystalline powder of melting point above 300° C., which has an active content (determined by UV spectrophotometry) of 93.4%. The yield of disodium 4,4'-dinitrostilbene-2,2'-disulfonate is 96.2% of theory. The yield of disodium 4,4'-dinitrostilbene-2,2'-disulfonic acid of the reaction mixture before workup as determined by LC analysis is 97.3% of theory.

EXAMPLE 13

In a glass autoclave according to Example 3, 97.7 g of 4-nitrotoluene-2-sulfonic acid (active content: 73.4%; water content: 18.2%; sulfuric acid content: 8.4%) and 1.6 g of manganese (II) acetate tetrahydrate are initially introduced at atmospheric pressure. The autoclave is sealed, and at an internal temperature of 20° C. to 24° C. 257 g of liquid ammonia are added over 35 minutes, resulting in an increase of the internal pressure to 5.6 bar. The reaction mixture is now treated with 64.8 g of 30% aqueous sodium hydroxide solution at an internal temperature of 10° C. to 15° over a period of 15 minutes.

An oxygen stream of 10 l/h is introduced above the level of the resulting clear solution at a stirrer speed of 600 to 700 r.p.m. In addition 21.3 g of a 30% aqueous sodium hydroxide solution are added over period of 20 minutes at an internal temperature of 15° C. to 20° C. The resulting reaction mixture contains an ammonia/water mixture of 77% of ammonia and 23% of water (this corresponds to a ratio of 1 part of p-NTSA to 4.7 parts of the solvent mixture). The resulting reaction mixture is stirred for 2 hours at 15° C., while oxygen (10 l/h) is introduced.

The workup is carried out as described in Example 1 except that the reaction mixture is treated with 8.6 g of ammonium chloride and is diluted with 100 ml of water instead of methanol. This gives 76.1 g of disodium 4,4'-dinitrostilbene-2,2'-disulfonate in the form of a light yellow crystalline powder of melting point above 300° C., which has an active content (determined by UV spectrophotometry) of 93.8%. The yield of disodium 4,4'-dinitrostilbene-2,2'-disulfonate is 94.0% of theory. The yield of disodium 4,4'-dinitrostilbene-2,2'-disulfonic acid of the reaction mixture before workup as determined by LC analysis is 94.5% of theory.

EXAMPLE 14

In a glass autoclave according to Example 3, 77.6 g of sodium 4-nitrotoluene-2-sulfonic acid (active content: 98.6%), 3.2 g of manganese (II) acetate tetrahydrate and 415 g of liquid methylamine are initially introduced at atmospheric pressure and at −10° C.—this corresponds to a ratio of 1 part of the sodium salt of p-NTSA to 5.5 parts of solvent.

An oxygen stream of 8 l/h is introduced above the level of the resulting clear solution at a stirrer speed of 1800 r.p.m. In addition, 28.8 g of a 30% methanolic sodium methylate solution are added over a period of 20 minutes at an internal temperature from −10° C. to −5° C. The resulting reaction mixture is stirred for an hour and 40 minutes at −10° C., while oxygen (8 l/h) is introduced.

The workup is carried out as described in Example 1 except that the reaction mixture is treated with 8.6 g of ammonium chloride and is diluted with 200 ml of methanol. This gives 61.5 g of disodium 4,4'-dinitrostilbene-2,2'-disulfonate in the form of a light yellow crystalline powder of melting point above 300° C., which has an active content (determined by UV spectrophotometry) of 92.3%. The yield of disodium 4,4'-dinitrostilbene-2,2'-disulfonate is 74.8% of theory.

What is claimed is:

1. A process for the preparation of 4,4'-dinitrostilbene-2,2'-disulfonic acid or a salt thereof of the formula

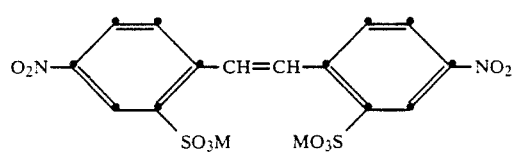

in which M is hydrogen, an alkali metal cation or an ammonium cation, by oxidation of 4-nitrotoluene-2-sulfonic acid or salts thereof with an oxidizing agent, which comprises performing the oxidation in liquid, anhydrous ammonia or in a primary, secondary or tertiary lower alkyl amine, in the absence or presence of water and/or mixtures of these solvents in one another with the proviso that the proportion of ammonia or a primary, secondary or tertiary lower alkylamine, in a mixture is 50% to 99%, and in the presence of a strong base.

2. A process according to claim 1, wherein the oxidation is carried out in a mixture of ammonia with water.

3. A process according to claim 1, wherein the base is used dissolved in a protic solvent.

4. A process according to claim 3, wherein the protic solvent used is a low-molecular-weight alcohol and/or water.

5. A process according to claim 1, wherein the strong base used is an alkali metal or alkaline earth metal compound.

6. A process according to claim 5, wherein the strong base used is a hydroxide or an alcoholate of an alkali metal or an alkaline earth metal or a mixture of these compounds or also a strongly basic ion-exchanger.

7. A process according to claim 1, wherein additionally a catalyst is used.

8. A process according to claim 7, wherein the catalyst used is a salt, oxide or hydroxide of a heavy metal compound and/or an organometallic compound of heavy metal.

9. A process according to claim 7, wherein the catalyst used is a phase transfer catalyst or a crown ether.

10. A process according to claim 1, wherein the oxidation is carried out at temperatures between $-33°$ C. and $+50°$ C.

11. A process according to claim 10, wherein the oxidation is carried out at temperatures between $-15°$ C. and 30° C.

12. A process according to claim 1, wherein 1 to 10 parts of ammonia or a primary, secondary or tertiary lower alkyl amine, in the absence or presence of water or a mixture thereof is used per part of 4-nitrotoluene-2-sulfonic acid.

13. A process according to claim 12, wherein 3 to 6 parts of ammonia or a primary, secondary or tertiary lower alkyl amine, in the absence or presence of water or a mixture thereof is used per part of 4-nitrotoluene-2-sulfonic acid.

14. A process according to claim 1, wherein the oxidizing agent used is pure oxygen or a mixture thereof with inert gases or is air.

15. A process according to claim 1, wherein 1 part of 4-nitrotoluene2-sulfonic acid or a salt thereof in the form of a moist presscake is suspended together with a catalytic amount of manganese (II) salt in 0.5 to 3 parts of aqueous ammonia solution or water and are treated with 1 to 5 parts of liquid ammonia, bringing the ammonia content of the entire reaction mixture to 60% to 80% and this mixture is reacted in the presence of oxygen as the oxidizing agent and sodium hydroxide as the base at temperatures from 0° to 25° C. and under pressure.

16. A process according to claim 1, wherein the proportion of ammonia or the primary, secondary or tertiary lower alkyl amine in a mixture with water is 60% to 80%.

* * * * *